(12) United States Patent
Kinsho et al.

(10) Patent No.: US 9,688,622 B1
(45) Date of Patent: Jun. 27, 2017

(54) 1-(2-ACYLOXYETHYL)CYCLOPROPYL SULFONATE COMPOUND, 3-HALOMETHYL-3-BUTENYL CARBOXYLATE COMPOUND, AND METHOD FOR PRODUCING 4-ALKYL-3-METHYLENEBUTYL CARBOXYLATE

(71) Applicant: Shin-Etsu Chemical Co., Ltd., Tokyo (JP)

(72) Inventors: Takeshi Kinsho, Joetsu (JP); Naoki Ishibashi, Joetsu (JP); Yusuke Nagae, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/436,320

(22) Filed: Feb. 17, 2017

Related U.S. Application Data

(62) Division of application No. 14/974,052, filed on Dec. 18, 2015, now Pat. No. 9,611,211.

(30) Foreign Application Priority Data

Dec. 25, 2014 (JP) .................. 2014-262613

(51) Int. Cl.
    *C07C 69/52* (2006.01)
    *C07C 309/66* (2006.01)
    *C07C 309/73* (2006.01)

(52) U.S. Cl.
    CPC .......... *C07C 309/66* (2013.01); *C07C 309/73* (2013.01); *C07C 2101/02* (2013.01)

(58) Field of Classification Search
    USPC ...................................... 560/205
    See application file for complete search history.

(56) References Cited

U.S. PATENT DOCUMENTS

| 3,388,192 A | 6/1968 | Machleidt et al. |
| 4,745,229 A | 5/1988 | Otera et al. |

FOREIGN PATENT DOCUMENTS

| GB | 2111501 A | 7/1983 |

OTHER PUBLICATIONS

Racouchot et al. European Journal of Organic Chemistry (2002), (13), 2160-2176.*
Kananovich et al, "A highly stereoselective transformation of carboxylic esters to trisubstituted olefins via cationic cyclopropyl-allyl rearrangement of sulfonates of cis-1,2-disubstituted cyclopropanols", Tetrahedron Letters 48:8424-8429 (2007).
Ochiai et al. "Iodine(III)-Mediated Allylation of Aromatic Compounds and Alcohols Using Allylmetal (Group 1Vb) Compounds", Chem. Pharm. Bull. 33(1):41-47 (1985).
Zaragoza Dörwald "Side Reactions in Organic Synthesis", Wiley-VCH Verlag GmbH & Co KGaA p. IX (2005).
Gieselmann et al. "Sex Pheromone of the San Jose Scale[1,2]", J. Chem. Ecol. 5(6):891-900 (1979).
Anderson et al. "Synthesis of 7-Methyl-3-Methylene-7-Octen-1-YL Propanoate and (Z)-3,7-Dimethyl-2,7-Octadien-1-YL Propanoate, Components of the Sex Pheromone of the San Jose Scale[1]", J. Chem. Ecol. 5(6)1419-927 (1979).
Weiler et al. "The synthesis of the isomeric comonents of San Jose scale pheromone—and illustration of a stereospecific synthesis of trisubstituted alkenes", Can. J. Chem. 71:1955-1963 (1993).
Weedon et al. "Photoenolisation of Conjugated Esters: Synthesis of a San Jose Scale Pheromone by Partially Regio-Controlled Photochemical Deconjugation[1]", Tetrahedron Letters 27(46):5555-5558 (1986).
Zhang et al. "Modification of Wolinsky's Ene-Chlorination", Chinese Chemical Letters 2(8):611-612 (1991).
Huaxue Tongbao pp. 40-42 (1994).
Chong et al. "Studies on the Alkylation of 3-Methyl-3-buten—1-ol Dianion: An Efficient Synthesis of 3-Methylene-1-alkanois including a San Jose Scale Sex Pheromone", J. Org. Chem. 66:8248-8251 (2001).
Veselovskii et al. "Synthesis of α-Myrcenol Acetate and Propionate from Isobutenylcarbinol", Izvestiya Akademii Nauk SSSR, Seriya Khimicheskaya 3:513-516 (1990).
Aldrich et al. "Identification of Presumed Pheromone Blend from Australasian Predaceous Bug, Oechalia schellengergii (Heteroptera: Pentatomidae)", J. Chem. Ecol. 22(4):729-738 (1996).
Kozyrkov et al. "A Simple and Efficient Conversion of Tertiary Cyclopropanols to 2-Substituted Allyl Halides", Synlett 3:443-446 (2002).
Kulinkovich et al. "A Convenient Way for the Conversion of Carboxylic Esters into 2-Substituted Allyl Halides", Synthesis 10:1713-1717 (2005).
European Search Report corresponding to European Application No. 15200348 dated Apr. 21, 2016.
Bailey et al. "Pyroiysis of Esters. XXI. 2-Hydroxymethyl-1,2-butadiene-[1,2]", J. Org. Chem. pp. 1975-1978 (1962).

(Continued)

Primary Examiner — Yong Chu
Assistant Examiner — Ana Z Muresan
(74) Attorney, Agent, or Firm — Myers Bigel, P.A.

(57) ABSTRACT

Provided is a 1-(2-acyloxyethyl)cyclopropyl sulfonate compound of General Formula (2):

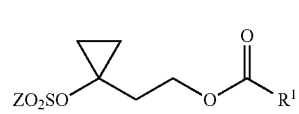

(2)

wherein $R^1$ is a monovalent hydrocarbon group having 1 to 10 carbon atoms and optionally containing one or more unsaturated bonds and Z is a monovalent hydrocarbon group having 1 to 10 carbon atoms and optionally containing one or more unsaturated bonds.

1 Claim, No Drawings

(56) References Cited

OTHER PUBLICATIONS

Ferraboschi et al. "Regio- and Enantioselectivity of *Pseudomonas cepacia* Lipase in the Transesterification of 2-Substituted-1,4-Butanediols", *Tetrahedron Asymmetry* 5(4):691-698 (1994).

Li et al. "Approaches to selective isoprenologation via reactions of $(\eta^3\text{-allyl})\text{Fe(CO)}^+_4$ with allyl nucleophiles", *J. Organometallic Chem.* 402:105-112 (1991).

Tabuchi et al. "Total Synthesis of Alternaric Acid", *Tetrahedron Letters* 34(14):2327-2330 (1993).

Wade et al. "Thermolytic Rearrangements of 1,1-Cyclopropanedimethanol Disulfonates: Cyclopropylcarbinyl Cations Revisited", *J. Org. Chem.* 58:3140-3147 (1993).

European Search Report corresponding to European Application No. 15200346 dated Apr. 20, 2016.

\* cited by examiner

US 9,688,622 B1

1-(2-ACYLOXYETHYL)CYCLOPROPYL SULFONATE COMPOUND, 3-HALOMETHYL-3-BUTENYL CARBOXYLATE COMPOUND, AND METHOD FOR PRODUCING 4-ALKYL-3-METHYLENEBUTYL CARBOXYLATE

RELATED APPLICATION

This application is a divisional application of U.S. application Ser. No. 14/974,052, filed Dec. 18, 2015, currently pending, which claims priority from Japanese Patent Application No. 2014-262613, filed Dec. 25, 2014, the disclosure of each of which is incorporated by reference herein in their entirety.

FIELD AND BACKGROUND OF THE INVENTION

The present invention relates to a method for producing a 4-alkyl-3-methylenebutyl carboxylate that is useful as a bioactive substance such as an insect pheromone and substance relating thereto and as a synthetic intermediate in organic synthetic chemistry. For example, the present invention relates to a method for producing 7-methyl-3-methylene-7-octenyl propionate, which is, for example, a major component of the sex pheromone of *Quadraspidiotus perniciosus* (Comstock) (generic name: San Jose Scale).

The sex pheromones of insects are biologically active substances that are commonly secreted by female individuals and have the function of attracting male individuals. A small amount of the sex pheromone shows strong attractive activities. The sex pheromone has been widely used as means for forecasting insect emergence or for ascertaining regional spread (invasion into a specific area) and as means for controlling an insect pest. As the means for controlling insect pests, control methods called mass trapping, lure and kill (another name: attract and kill), lure and infect (another name: attract and infect), and mating disruption are widely used in practice. To utilize the sex pheromone, economical production of a required amount of the pheromone product is demanded for basic research and also for application.

*Quadraspidiotus perniciosus* (generic name: San Jose Scale, hereinafter abbreviated as "SJS") is widely distributed in the world, damages fruit trees and ornamental trees, especially deciduous fruit trees, and thus is an economically critical insect pest. As for the sex pheromone of SJS, three compounds of 7-methyl-3-methylene-7-octenyl propionate, (Z)-3,7-dimethyl-2,7-octadienyl propionate, and (E)-3,7-dimethyl-2,7-octadienyl propionate have been identified as the active components by Gieselmann et al. (J. Chem. Ecol., 5, 891 (1979)).

These sex pheromone compounds of SJS are isomers to each other, and there is a demand for a selective production method of each compound for basic biological studies and agronomic studies. There is also a strong demand for an efficient production method capable of supplying a sufficient amount of the pheromone product for the purposes of application and practical use.

Examples of the synthesis of 7-methyl-3-methylene-7-octenyl propionate, which is the major component of the sex pheromone of SJS, include the following Syntheses (a) to (f):

Synthesis (a) comprising addition of an organocuprate reagent to alkyne as a key reaction, by Anderson et al. (J. Chem. Ecol., 5, 919 (1979));

Synthesis (b) comprising a one-carbon homologation step of a β-keto ester compound, 7-methyl-3-oxo-7-octenoate, by Weiler et al. (Can. J. Chem., 71, 1955 (1993));

Synthesis (c) comprising photochemical position isomerization of a double bond of an α,β-unsaturated ester to a β,γ-unsaturated ester as a key reaction, by Weeden et al. (Tet. Lett., 27, 5555 (1986));

Synthesis (d) comprising exo-methylene formation as a key reaction by reduction of an allylic chloride obtained by chlorination involving isomerization of a trisubstituted double bond, by Zhang et al. (Chinese Chemical Letters, 2, 611 (1991), Huaxue Tongbao, 40, (1994));

Synthesis (e) by alkylation of a dianion of 3-methyl-3-buten-1-ol, by Anderson et al. (J. Chem. Ecol., 5, 919 (1979)) and Chong et al. (J. Org. Chem., 66, 8248 (2001)); and Synthesis (f) which is a nonselective synthesis through an allylic chloride mixture, by Veselovskii et al. (Izvestiya Akademii Nauk SSSR, Seriya Khimicheskaya, 3, 513 (1990)).

SUMMARY OF THE INVENTION

These synthetic methods unfortunately involve a lot of difficulties in order to selectively synthesize 7-methyl-3-methylene-7-octenyl propionate in a high yield on an industrial scale. For example, the difficulties arise from the use of reagents that are expensive or difficult to handle on an industrial scale, including an organolithium reagent such as n-butyllithium and methyllithium in Syntheses (b) and (e), lithium aluminum hydride (LAH) in Syntheses (a), (b) and (d), a stoichiometric amount of an organocuprate reagent in Synthesis (a), a Tebbe reagent in Synthesis (b), and sulfuryl chloride in Synthesis (f). In the synthetic route in which a double bond is intentionally isomerized even by the photochemical isomerization in Synthesis (c) or the isomerization through an allylic chloride in Synthesis (d), undesired isomers are unfortunately formed in small amounts as by-products and thus are required to be removed even if the isomerization is achieved with a comparatively high selectivity. The synthesis in Synthesis (f), in which unintended isomers are mixed with a synthetic intermediate, also has significant problems because a target compound is difficult to separate from isomers thereof and the yield is lowered. In Syntheses (a) to (f), intermediates and a target compound are isolated or purified by various types of chromatography, which are difficult to perform on an industrial scale. As described above, the existing syntheses are considered to be very difficult to economically produce a sufficient amount of the product on an industrial scale.

In view of the above circumstances, an object of the present invention is to provide a simple, selective and efficient production method in order to supply sufficient amounts of 4-alkyl-3-methylenebutyl carboxylates such as 7-methyl-3-methylene-7-octenyl propionate, which is a major component of the sex pheromone of SJS, the component being required for biological studies, agronomic studies, actual application and utilization, and the like.

As a result of intensive studies, the inventors of the present invention have found that by selecting reagents and conditions that can be easily achieved on an industrial scale, 4-alkyl-3-methylenebutyl carboxylate compounds can be synthesized with a high selectivity, and have completed the present invention.

In an aspect of the present invention, there is provided a method for producing a 4-alkyl-3-methylenebutyl carboxylate compound, the method comprising an acyloxylation step of subjecting a 1-(2-haloethyl)cyclopropyl sulfonate compound represented by General Formula (1) to acyloxylation to obtain a 1-(2-acyloxyethyl)cyclopropyl sulfonate compound represented by General Formula (2), a halogenation step of subjecting the 1-(2-acyloxyethyl)cyclopropyl sulfonate compound (2) to halogenation involving cyclopropyl-allyl rearrangement to obtain a 3-halomethyl-3-butenyl carboxylate compound represented by General Formula (3), and a coupling step of subjecting the 3-halomethyl-3-butenyl carboxylate compound (3) to a coupling reaction with an organometallic reagent represented by General Formula (4) to obtain the 4-alkyl-3-methylenebutyl carboxylate compound represented by Formula (5).

In General Formulae below, $X^1$ and $X^2$ may be the same or different and each represents a halogen atom; $R^1$ and $R^2$ may be the same or different and each represents a monovalent hydrocarbon group having 1 to 10 carbon atoms and optionally containing one or more unsaturated bonds; Z represents a monovalent hydrocarbon group having 1 to 10 carbon atoms and optionally containing one or more unsaturated bonds and; M represents a cationic moiety.

In another aspect of the present invention, there is provided a 1-(2-acyloxyethyl)cyclopropyl sulfonate compound (2).

In still another aspect of the present invention, there is provided a 4-halo-3-methylenebutyl carboxylate compound represented by General Formula (3b). In General Formula (3b), $X^3$ is a bromine atom or an iodine atom.

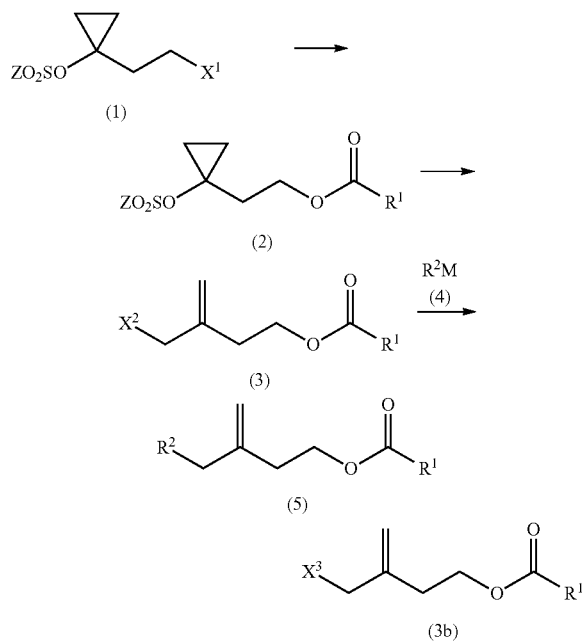

According to the present invention, a 4-alkyl-3-methylenebutyl carboxylate compound such as 7-methyl-3-methylene-7-octenyl propionate can be selectively and efficiently synthesized through useful intermediates, a 1-(2-acyloxyethyl)cyclopropyl sulfonate compound and a 3-halomethyl-3-butenyl carboxylate compound.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

The chemical formulae of intermediates, reagents and target compounds in the present specification can include isomers that differ in substitution sites and stereoisomers such as enantiomers and diastereomers in terms of structure. Unless otherwise stated, each chemical formula is intended to represent all the isomers in each case. Each of these isomers may be used singly or in combination of two or more.

The inventors of the present invention have considered the synthetic route of 4-alkyl-3-methylenebutyl carboxylate compounds as follows: One of the target 4-alkyl-3-methylenebutyl carboxylate compounds, 7-methyl-3-methylene-7-octenyl propionate (A), which is a major component of the sex pheromone of SJS, will be described as an example. In order to build the carbon framework having 10 carbon atoms of the target compound (A) in consideration of easy availability and cost efficiency of raw materials, if two building blocks each having 5 carbon atoms in the below formula can be used to form a bond, in other words, if an organometallic reagent (B) as a nucleophile and an electrophile (C) having 5 carbon atoms and having a leaving group L and a propionyloxy group, which is a functional group present on the target compound, can undergo a coupling reaction in such a manner that the leaving group L is eliminated, it is considered that a straightforward and efficient synthesis can be achieved through a short process.

It is considered that the electrophile (C) can be prepared from a known 1-(2-haloethyl)cyclopropanol compound (D) by performing the following reactions that are combined in an appropriate order: (1) sulfonylation of the hydroxy group; (2) a halogenation reaction involving cyclopropyl-allyl rearrangement of the obtained cyclopropyl sulfonate; and (3) a propionyloxylation reaction of the halogen group X into propionate.

In the following reaction equation, the hollow arrows represent transformation in a retrosynthetic analysis, L represents a leaving group, and M represents a cationic moiety. The small numeric characters attached on the compound (C) represent the position numbers of carbons.

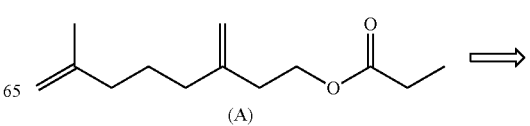

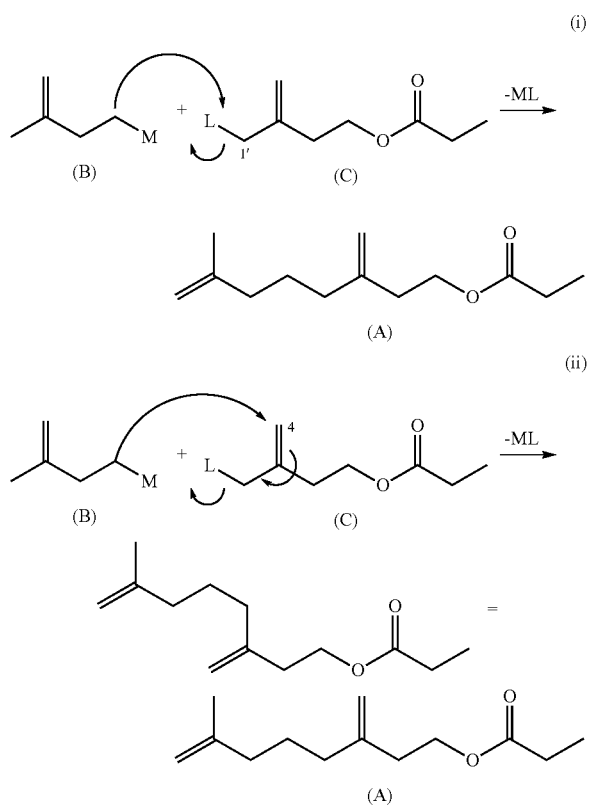

In the retrosynthetic analysis, it is important to achieve the selectivity of the coupling reaction between the nucleophile (B) and the electrophile (C). The reaction sites in the electrophile (C) capable of forming a carbon-carbon bond with the nucleophile (B) can be the carbons at the 1-position, the 1'-position, and the 4-position. Shown below are the reaction scheme (i) in which the carbon at the 1'-position of the electrophile (C) undergoes the coupling reaction, the reaction scheme (ii) in which the carbon at the 4-position undergoes the coupling reaction, the reaction scheme (iii) in which the carbon at the 1-position undergoes the coupling reaction, and the reaction scheme (iv) in which an addition reaction occurs at the carbonyl group of the propionyloxy group.

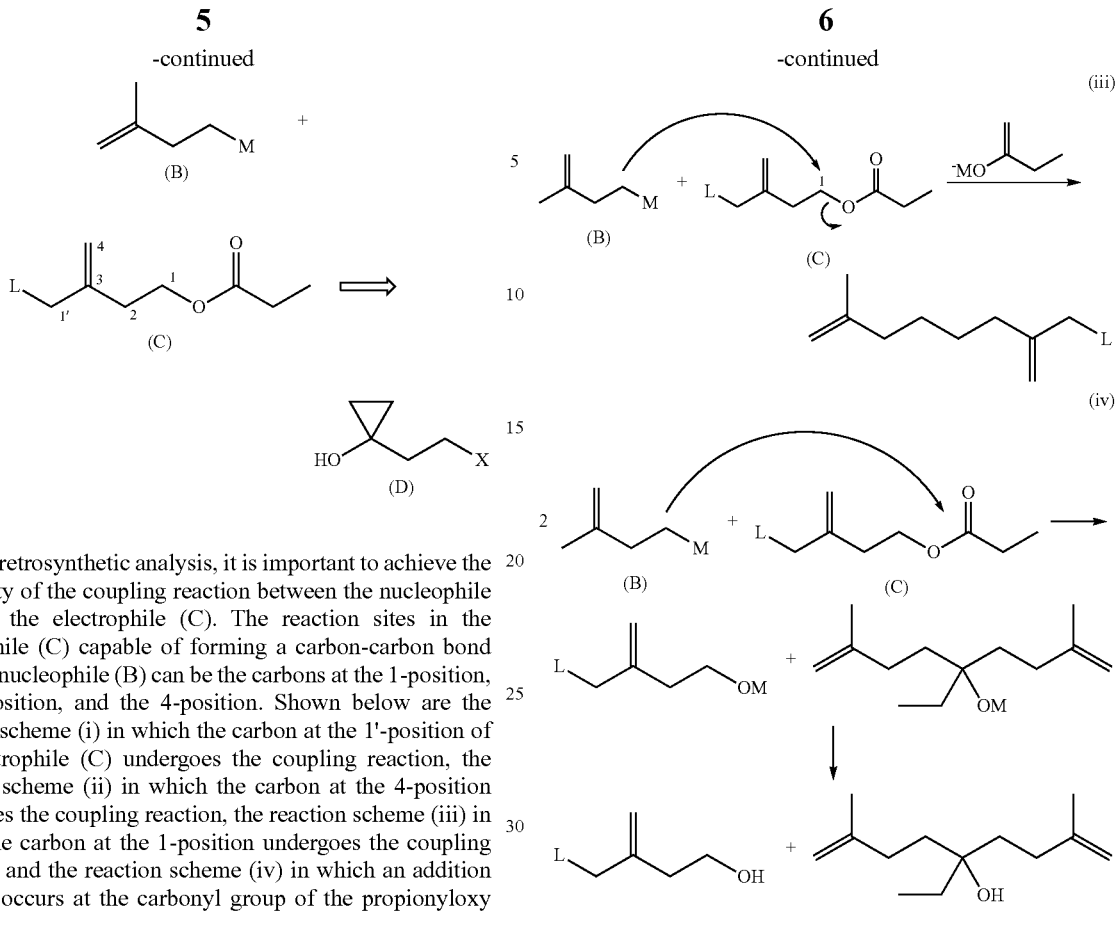

In the reaction scheme (i), a nucleophilic attack occurs at the carbon at the 1'-position to lead to the $S_N2$ reaction (bimolecular nucleophilic substitution reaction), and L is eliminated to obtain the target compound (A). In the reaction scheme (ii), a nucleophilic attack occurs at the carbon at the 4-position to lead to a substitution reaction involving allylic rearrangement that is called an $S_N2'$ reaction. Also in this scheme, L is expected to be eliminated to obtain the same target compound (A).

On the other hand, in the reaction scheme (iii), it is supposed that a nucleophilic attack occurs at the carbon at the 1-position and the propionyloxy group is eliminated to give a product that differs from the target compound (A). In the reaction scheme (iv), it is supposed that the addition reaction proceeds at the carbonyl group of the propionyloxy group to give a product that differs from the target compound (A). In addition, when the leaving group L is an acyloxy group, the carbonyl group of the acyloxy group provides a product that differs from the target compound (A).

From the above consideration, the selectivity of advancing the coupling reaction in which a nucleophilic attack occurs at the carbon at the 1'-position or the carbon at the 4-position of the electrophile (C) to eliminate the leaving group L prior to the coupling reaction at the 1-position and prior to the addition reaction to a carbonyl group is preferably achieved for the purpose. In the synthetic strategy, the leaving group L at the 1'-position and the propionyloxy group at the 1-position in the compound (C) differ in the substitution positional relation with regard to the double bond. In other words, the leaving group L is at an allylic position, while the propionyloxy group is at a homoallylic position. It is thus considered that the intended selectivity can be achieved by selecting the type of the leaving group L and reaction conditions.

As a result of repeated studies based on the above consideration, an efficient synthesis having an intended high selectivity has been achieved. Embodiments of the present invention will now be described in detail. It should not be construed that the present invention is limited to or by them.

According to the invention, a 1-(2-haloethyl)cyclopropyl sulfonate compound (1) as the starting material can be obtained, for example, by sulfonylation of a 1-(2-haloethyl) cyclopropanol in accordance with the document (Kulinkovich et. al., Synthesis, 2005, 1713), as shown in the following reaction equation.

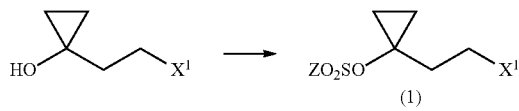

(1)

$X^1$ represents a halogen atom, and Z represents an alkyl group having 1 to 10 carbon atoms or an aryl group having 6 to 10 carbon atoms, the alkyl or aryl group optionally containing one or more unsaturated bonds. The halogen atom includes a chlorine atom, a bromine atom, and an iodine atom.

Z is a monovalent hydrocarbon group having 1 to 10 carbon atoms and optionally containing one or more unsaturated bonds and is preferably an alkyl group having 1 to 10 carbon atoms or an aryl group having 6 to 10 carbon atoms, the alkyl or aryl group optionally containing one or more unsaturated bonds. The alkyl group having 1 to 10 carbon atoms is a chain, branched or cyclic monovalent hydrocarbon group and is preferably a linear saturated alkyl group such as a methyl group, an ethyl group, an n-propyl group and an n-butyl group. Examples of the aryl group having 6 to 10 carbon atoms include a phenyl group, a tolyl group, a xylyl group and a naphthyl group. Specifically preferred examples of Z include a methyl group, an n-butyl group, a phenyl group and a p-tolyl group.

Next, the acyloxylation reaction step of subjecting the 1-(2-haloethyl)cyclopropyl sulfonate compound (1) to acyloxylation to obtain a 1-(2-acyloxyethyl)cyclopropyl sulfonate compound (2) will be described.

In the following reaction equation, $R^1$ is a monovalent hydrocarbon group having 1 to 10 carbon atoms and optionally containing one or more unsaturated bonds.

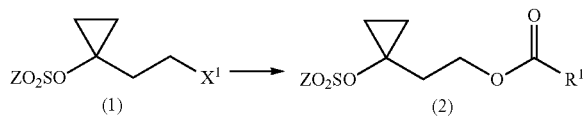

As for the synthesis of the intermediate 1-(2-acyloxyethyl)cyclopropyl sulfonate compound (2), the method in accordance with the present invention in which an acyloxylation step and the subsequent halogenation step involving arrangement are carried out in this order, is preferred in terms of ease in extraction of the intermediate and the yield as compared with another possible method in which a halogenation step involving arrangement and the subsequent acyloxylation step are carried out in this order, more specifically, as compared with the method comprising the steps of: subjecting a halogenated 1-(2-haloethyl)cyclopropanol to acyloxylation to obtain a 1-(2-acyloxyethyl)cyclopropanol, and subjecting the 1-(2-acyloxyethyl)cyclopropanol to sulfonylation to obtain the 1-(2-acyloxyethyl)cyclopropyl sulfonate compound (2).

In addition, in the synthesis of the intermediate 1-(2-acyloxyethyl)cyclopropyl sulfonate compound (2), a nucleophilic substitution reaction occurs only at the leaving group $X^1$ on the methylene chain, while the sulfonyloxy group that is the leaving group on cyclopropane is not affected in absence of side reactions such as elimination and substitution. Thus, the functional group selectivity is achieved. In other words, the intermediate is designed so as to achieve the functional group selectivity.

$X^1$ represents a halogen atom and is preferably a chlorine atom, a bromine atom, or an iodine atom.

$R^1$ represents a chain, branched or cyclic monovalent hydrocarbon group having 1 to 10 carbon atoms and optionally containing one or more unsaturated bonds. $R^1$ may be selected to be a group corresponding to the structure of a final target compound of the synthesis. Examples of $R^1$ include linear monovalent hydrocarbon groups such as a methyl group, an ethyl group, a n-propyl group, a n-butyl group, a n-pentyl group, a n-hexyl group, a n-heptyl group, a n-octyl group, a n-nonyl group, a n-decyl group, a vinyl group, a 1-propenyl group, an allyl group, a 1-butenyl group, a 2-butenyl group, a 3-butenyl group, a 1-pentenyl group, a 2-pentenyl group, a 5-hexenyl group, a 1-heptenyl group, a 9-decenyl group, a 1,3-butadienyl group, a 1,3-pentadienyl group, a 1,5-hexadienyl group and an ethynyl group; branched monovalent hydrocarbon groups such as an isopropyl group, a 2-ethylpropyl group, a t-butyl group, a sec-butyl group, an isobutyl group, a t-amyl group, a neopentyl group, a 1-methylbutyl group, a 1-propylbutyl group, a 2-methylbutyl group, a 3-methylbutyl group, a 1-methylpentyl group, a 1-ethylpentyl group, an isopropenyl group, a 1-methyl-1-propenyl group, a 2-methyl-1-propenyl group, a 1-methyl-1-butenyl group, a 1,1-dimethyl-3-butenyl group, a 1-ethyl-1-pentenyl group, a 2,6-dimethyl-5-heptenyl group, a 2,6-dimethyl-1,5-heptadienyl group, a 2,6-dimethyl-1,6-heptadienyl group, a 6-methyl-2-methylene-5-heptenyl group, a 6-methyl-2-methylene-6-heptenyl group, a 4-methyl-1-pentenyl-3-pentenyl group and a 1-isopropylidene-4-methyl-3-pentenyl group; and cyclic monovalent hydrocarbon groups such as a cyclopropyl group, a 2-methylcyclopropyl group, a 2,2,3,3-tetramethylcyclopropyl group, a cyclobutyl group, a cyclopentyl group, a cyclopentylmethyl group, a 2-cyclopentylethyl group, a cyclohexyl group, a cyclohexylmethyl group, a dicyclohexylmethyl group, a 2-cyclohexylethyl group, a 3-cyclohexylpropyl group, a 4-cyclohexylbutyl group, a 1-methylcyclohexyl group, a 2-methylcyclohexyl group, a 3-methylcyclohexyl group, a 4-methylcyclohexyl group, a cycloheptyl group, a norbornyl group, a norbornylmethyl group, an isobornyl group, a menthyl group, a fenchyl group, an adamantyl group, a 1-cyclopentenyl group, a 2-cyclopentenyl group, a 1-cyclohexenyl group, a 1-methyl-2-cyclohexenyl group, a 2-methyl-2,5-dicyclohexadienyl group, a phenyl group, a benzyl group, a 1-phenylcyclopropyl group, a 2-phenylcyclopropyl group, a 1-phenylcyclopentyl group, a 1-phenylethyl group, a 2-phenylethyl group, a 1-methyl-2-phenylethyl group, a 1-phenylpropyl group, a 2-phenylpropyl group, a 3-phenylpropyl group, a 4-phenylbutyl group, a 1,2,3,4-tetrahydro-2-naphthyl group, a 2-phenylethenyl group, a 3-phenyl-2-propenyl group, a 1-methyl-3-phenylethenyl group, a p-tolyl group, an m-tolyl group, an o-tolyl group, a 4-ethylphenyl group, a 4-propylphenyl group, a 4-isopropylphenyl group, a 4-butylphenyl group, a 4-t-butylphenyl group, a 1-naphthyl group and a 2-naphthyl group.

The acyloxylation reaction is typically carried out by stirring the 1-(2-haloethyl)cyclopropyl sulfonate compound (1) together with a salt of a carboxylic acid ($R^1COOH$) having corresponding $R^1$ in a solvent.

Examples of the carboxylate salt in the acyloxylation reaction include various metal salts and onium salts, and preferably include lithium salts, sodium salts, potassium salts, magnesium salts, calcium salts, ammonium salts, tetraalkylammonium salts and tetraalkylphosphonium salts.

The amount of the carboxylate salt may be freely selected in consideration of various conditions and is preferably 0.2 to 100 mol, more preferably 1 to 20 mol, even more preferably 1 to 10 mol relative to 1 mol of the 1-(2-haloethyl)cyclopropyl sulfonate compound (1). The amount is preferably 1 mol or more from the viewpoint of yield. The amount may be more than 1 mol because studies have revealed that typically only under severe conditions, a carboxylate ion ($RCOO^-$) causes acyloxylation involving cyclopropyl-allyl rearrangement as a side reaction to generate a 4-acyloxy-3-methylenebutyl carboxylate compound or a 4-halo-2-methylenebutyl carboxylate compound as a by-product.

Examples of the solvent to be used for the acyloxylation reaction preferably include carboxylic acids such as formic acid, acetic acid, propionic acid and a carboxylic acid ($R^1COOH$) having corresponding $R^1$; carboxylic anhydrides such as acetic anhydride, propionic anhydride and carboxylic anhydrides ($R^1CO—O—COR^1$) having corresponding $R^1$; esters such as methyl formate, ethyl formate, methyl acetate, ethyl acetate, and methyl esters, ethyl esters, n-propyl esters and n-butyl esters of carboxylic acids having corresponding $R^1$; ethers such as diethyl ether, di-n-butyl ether, t-butyl methyl ether, cyclopentyl methyl ether, tetrahydrofuran and 1,4-dioxane; hydrocarbons such as hexane, heptane, benzene, toluene, xylene and cumene; chlorinated solvents such as dichloromethane, chloroform, tetrachloromethane, 1,2-dichloroethane and 1,1,2-trichloroethane, and aprotic polar solvents such as N,N-dimethylformamide (DMF), N,N-dimethylacetamide (DMAC), N,N-dimethylpropionamide, 1,3-dimethyl-2-imidazolidinone (DMI), dimethyl sulfoxide (DMSO) and hexamethylphosphoric triamide (HMPA). The solvent is used singly or in combination of two or more. The amount of the solvent is not particularly limited values and is preferably 0.1 part to 1,000,000 parts, more preferably 1 part to 100,000 parts, even more preferably 10 parts to 10,000 parts relative to 100 parts of the 1-(2-haloethyl)cyclopropyl sulfonate compound (1).

When a 1-(2-chloroethyl)cyclopropyl sulfonate compound or a 1-(2-bromoethyl)cyclopropyl sulfonate compound is used as the 1-(2-haloethyl)cyclopropyl sulfonate compound (1) in the acyloxylation reaction, an iodide salt such as lithium iodide, sodium iodide, potassium iodide, magnesium iodide, calcium iodide, ammonium iodide, tetraalkylammonium iodide and tetraalkylphosphonium iodide may be added to the reaction system, preferably in an amount of 0.0001 to 5 mol relative to 1 mol of the 1-(2-haloethyl)cyclopropyl sulfonate compound (1), so that the reaction may be carried out while generating a 1-(2-iodoethyl)cyclopropyl sulfonate compound in situ. Alternatively, the 1-(2-iodoethyl)cyclopropyl sulfonate compound can be prepared in advance and then may undergo the reaction.

In the acyloxylation reaction, a silver salt such as silver nitrate may also be added preferably in an amount of 0.0001 to 5 mol relative to 1 mol of the 1-(2-haloethyl)cyclopropyl sulfonate compound (1) so that the resulting halide ion may be crystallized and precipitated as a silver salt (into a specific area) to accelerate the reaction.

The reaction temperature for the acyloxylation reaction is preferably 0° C. to the boiling point temperature of a solvent, more preferably 20 to 100° C. The reaction time can be freely selected and is preferably optimized by tracking the progress of the reaction by gas chromatography (GC) or thin-layer chromatography (TLC). Typically, the reaction time is preferably 5 minutes to 240 hours.

As a side reaction of the nucleophilic substitution acyloxylation reaction, an elimination reaction of a hydrogen halide may occur competitively to form 1-vinylcyclopropyl sulfonate as a by-product. Although the portion of this elimination reaction is commonly small, various reaction conditions are preferably selected so as to decrease the elimination reaction and to increase the intended substitution reaction, which is the ester formation reaction.

When the target 1-(2-acyloxyethyl)cyclopropyl sulfonate compound (2) obtained by the above acyloxylation reaction has sufficient purity, the crude product may be subjected to the subsequent step without purification, or may be purified by a method appropriately selected from purification methods commonly used in organic synthesis, such as distillation and various types of chromatography.

Next, the halogenation reaction step of subjecting the 1-(2-acyloxyethyl)cyclopropyl sulfonate compound (2) to halogenation involving cyclopropyl-allyl rearrangement to obtain a 3-halomethyl-3-butenyl carboxylate compound (3) will be described.

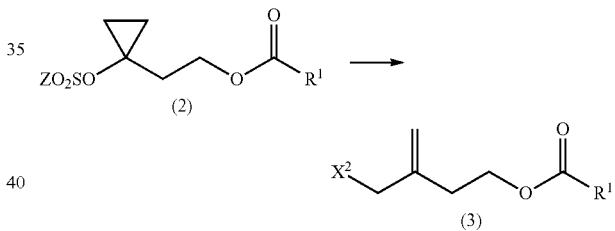

$X^2$ represents a halogen atom and is preferably a chlorine atom, a bromine atom, or an iodine atom.

The halogenation reaction is typically carried out by stirring the 1-(2-acyloxyethyl)cyclopropyl sulfonate compound (2) together with a metal salt having $X^2$ as an anionic moiety in a solvent.

The salt having $X^2$ as the anionic moiety is preferably a metal salt having Lewis acidity. Examples of the metal salt include magnesium salts, calcium salts, titanium salts, zirconium salts, iron salts, cobalt salts, nickel salts, copper salts, boron salts, aluminum salts, gallium salts, germanium salts and tin salts, and particularly preferably include magnesium salts, titanium salts, zirconium salts, aluminum salts and tin salts.

The amount of the metal salt can be freely selected in consideration of various conditions and is preferably 0.2 to 100 mol, more preferably 1 to 20 mol, even more preferably 1 to 10 mol relative to 1 mol of the 1-(2-acyloxyethyl)cyclopropyl sulfonate compound (2), in terms of mole number of the halogen moiety $X^2$ to be reacted. The metal salt is preferably used in an amount of 1 mol or more from the viewpoint of yield.

Examples of the solvent to be used for the halogenation reaction preferably include ethers such as diethyl ether, di-n-butyl ether, t-butyl methyl ether, cyclopentyl methyl ether, tetrahydrofuran and 1,4-dioxane; hydrocarbons such as hexane, heptane, benzene, toluene, xylene and cumene; chlorinated solvents such as dichloromethane, chloroform, tetrachloromethane, 1,2-dichloroethane and 1,1,2-trichloroethane; and aprotic polar solvents such as N,N-dimethylformamide (DMF), N,N-dimethylacetamide (DMAC), N,N-dimethylpropionamide, 1,3-dimethyl-2-imidazolidinone (DMI), dimethyl sulfoxide (DMSO) and hexamethylphosphoric triamide (HMPA). The solvent is used singly or in combination of two or more.

The amount of the solvent is not particularly limited and is preferably 0.1 part to 1,000,000 parts, more preferably 1 part to 100,000 parts, even more preferably 10 parts to 10,000 parts relative to 100 parts of the 1-(2-acyloxyethyl) cyclopropyl sulfonate compound (2).

The reaction temperature during the halogenation reaction is preferably 0° C. to the boiling point temperature of a solvent, more preferably 20 to 100° C. The reaction time can be freely selected and is preferably optimized by tracking the progress of the reaction by gas chromatography (GC) or thin-layer chromatography (TLC). Typically, the reaction time is preferably 5 minutes to 240 hours.

When the target 3-halomethyl-3-butenyl carboxylate compound (3) obtained by the halogenation reaction has sufficient purity, the crude product may be subjected to the subsequent step without purification, or may be purified by a method appropriately selected from purification methods commonly used in organic synthesis, such as distillation and various types of chromatography.

By the above synthetic method of the 3-halomethyl-3-butenyl carboxylate compound (3) as an electrophile, the target compound (3) is obtained in a high yield as substantially a single product in many cases. A 4-halo-3-methyl-2-butenyl carboxylate or a 4-halo-3-methyl-3-butenyl carboxylate, which is an impurity generated by positional isomerization of the double bond, is hardly formed as a by-product. Due to this high selectivity, the synthetic method has advantages over conventional methods such as the method of halogenation at an allylic position of olefin by using sulfuryl chloride ($SO_2Cl_2$) described in Veselovskii et al. Izvestiya Akademii Nauk SSSR, Seriya Khimicheskaya, 3, 513 (1990).

The 3-halomethyl-3-butenyl carboxylate compound (3) as an electrophile synthesized as above can be subjected to a coupling reaction with a nucleophile (4) to obtain a target 4-alkyl-3-methylenebutyl carboxylate compound (5).

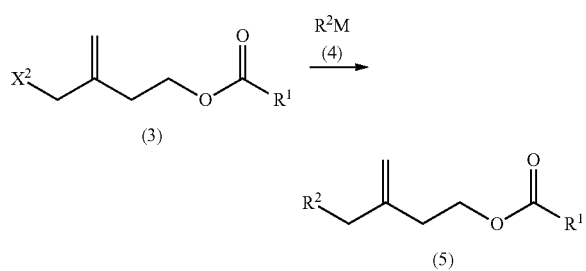

$R^2$ may be the same as or different from $R^1$ and is a chain, branched, or cyclic monovalent hydrocarbon group having 1 to 10 carbon atoms and optionally containing one or more unsaturated bonds. $R^2$ may be selected to be a group corresponding to the structure of a final target compound of the synthesis. Examples of $R^2$ may include the same groups as those for $R^1$.

In the present specification, as for the substituent name of $R^2$, there is no appropriate name for a monovalent substituent in which any hydrogen atom of a hydrocarbon is replaced by a bond, so that the name of an "alkyl" group corresponding to a monovalent substituent in which any hydrogen atom of the corresponding alkane is replaced by a bond is also used as the name for the monovalent substituent in which any hydrogen atom of a hydrocarbon is replaced by a bond, for convenience. Accordingly, the compound (5) is called a 4-alkyl-3-methylenebutyl carboxylate.

By appropriately selecting the conditions in the coupling reaction step, the coupling reaction at an allylic carbon having the leaving group $X^2$ in the compound (3) can be advanced prior to the coupling reaction at a homoallylic carbon having the $R^1COO$ group in the compound (3). Consequently, the target 4-alkyl-2-methylenebutyl carboxylate compound (5) can be obtained in a high yield.

Examples of the nucleophile (4) to be used in the coupling reaction step may include an organometallic reagent containing a group I or group II metal element or a transition metal element and having $R^2$ corresponding to the structure of a target compound.

Examples of the organometallic reagent containing a group I or group II metal element preferably include an organolithium reagent and an organomagnesium reagent (Grignard reagents) from the viewpoint of reactivity, selectivity, ease in preparation, and the like.

The organometallic reagent containing a transition metal element may be prepared by a metal exchange reaction using a stoichiometric amount (1 mol) or more of a transition metal compound with respect to 1 mol of an organolithium reagent or an organomagnesium reagent, or may be formed in situ from an organolithium reagent or a Grignard reagent with a transition metal compound catalyst. Examples of the transition metal compound may include transition metal compounds containing copper, iron, nickel, palladium, zinc, silver or the like, and particularly preferably include copper compounds such as copper(I) chloride, copper(I) bromide, copper(I) iodide, copper(I) cyanide, copper(I) oxide, copper (II) chloride, copper(II) bromide, copper(I) iodide, copper (II) cyanide, copper(II) oxide and dilithium tetrachlorocuprate ($Li_2CuCl_4$). The amount of the transition metal compound is from a catalytic amount (0.0001 to 0.999 mol) to a stoichiometric amount (1 mol) or an excess amount (more than 1 mol but not greater than 100 mol) relative to 1 mol of an organolithium reagent or an organomagnesium reagent. A catalytic amount of the transition metal compound is particularly preferably used.

Specifically, the cationic moiety M in the nucleophile (4) is particularly preferably Li, MgQ, ZnQ, Cu, CuQ, or CuLiQ wherein Q represents a halogen atom or $R^2$.

The organometallic reagent to be used as the nucleophile (4) is typically prepared from a halide containing corresponding $R^2$ in a usual manner. The halide is preferably a chloride, a bromide or an iodide.

The amounts of the nucleophile (4) and the electrophile (3) to be used for the coupling reaction may be freely selected in consideration of the types of the substrates, conditions, the reaction yield, and cost efficiency such as the prices of intermediates. The nucleophile (4) is preferably used in an amount of 0.2 to 10 mol, more preferably 0.5 to 2 mol, even more preferably 0.8 to 1.5 mol relative to 1 mol of the electrophile (3). However, after the formation of the target compound, there is a possibility that the addition reaction of the nucleophile (4) to the carbonyl group of the $R^1COO$ group in the target compound (5) may further proceed. When the conditions are used in which such a side reaction proceeds, it is preferable to avoid the use of the nucleophile (4) in an excess amount of greatly more than 1 mol relative to 1 mol of the electrophile (3).

Examples of the solvent to be used for the coupling reaction preferably include ethers such as diethyl ether, di-n-butyl ether, t-butyl methyl ether, cyclopentyl methyl ether, tetrahydrofuran and 1,4-dioxane. The solvent may be a mixed solvent of one or more ethers with one or more selected from hydrocarbons such as hexane, heptane, benzene, toluene, xylene and cumene and aprotic polar solvents such as N,N-dimethylformamide (DMF), N,N-dimethylacetamide, N,N-dimethylpropionamide, 1,3-dimethyl-2-imidazolidinone (DMI), dimethyl sulfoxide (DMSO) and hexamethylphosphoric triamide (HMPA). The amount of the solvent is not particularly limited and is preferably 0.1 part to 1,000,000 parts, more preferably 1 part to 100,000 parts, even more preferably 10 parts to 10,000 parts relative to 100 parts of the electrophile (3).

As the catalyst to be used for the coupling reaction, a lithium salt such as lithium chloride, lithium bromide and lithium iodide may be used in an amount of 0.0001 to 5 mol relative to 1 mol of the electrophile (3).

The reaction temperature for the coupling reaction is preferably −78° C. to the boiling point temperature of a solvent, more preferably −10° C. to 100° C. The reaction time may be freely selected and is preferably optimized by tracking the progress of the reaction by gas chromatography (GC) or thin-layer chromatography (TLC). Typically, the reaction time is preferably 5 minutes to 240 hours.

The target 4-alkyl-2-methylenebutyl carboxylate compound (5) obtained by the above coupling reaction may be purified by a method appropriately selected from purification methods commonly used in organic synthesis, such as distillation and various types of chromatography. Distillation is particularly preferred from the viewpoint of industrial cost efficiency.

As described above, a simple and efficient method for producing a 4-alkyl-2-methylenebutyl carboxylate compound (5) such as 7-methyl-3-methylene-7-octenyl propionate, which is the sex pheromone of SJS, is provided to supply a sufficient amount of the product for application and utilization.

EXAMPLES

The present invention will next be described in further detail with reference to Examples. It should not be construed that the present invention is limited to or by them.

In the following description, as the purities of raw materials, products and intermediates, the values obtained by gas chromatographic (GC) analyses are used and expressed as % GC. GC conditions were as follows: a gas chromatograph of Shimazdu GC-14A, a column of 5% Ph-Me silicone having 0.25 mmϕ×25 m, a carrier gas of helium and a flame ionization detector (FID) were used.

The crude products were optionally purified to obtain the samples for spectrum measurement.

Synthesis of 1-(2-acyloxyethyl)cyclopropyl sulfonate compound represented by General Formula (2)

Example 1: Synthesis 1 of 1-(2-propionyloxyethyl)cyclopropyl methanesulfonate which is the compound having Z=CH₃ and R¹=CH₃CH₂ in General Formula (2)

As shown in the following reaction equation, 1-(2-propionyloxyethyl)cyclopropyl methanesulfonate is synthesized from 1-(2-chloroethyl)cyclopropyl methanesulfonate.

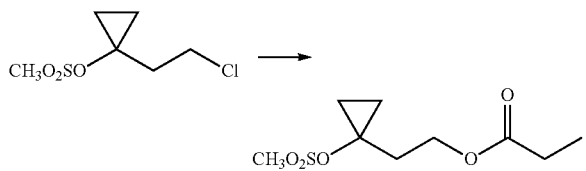

Under a nitrogen atmosphere, a mixture of 13.0 g of 1-(2-chloroethyl)cyclopropyl methanesulfonate (90.3% GC), 12.6 g of sodium propionate, 2.0 g of sodium iodide and 70 ml of N,N-dimethylacetamide was stirred at 90 to 100° C. for 5 hours. The reaction mixture was cooled on ice, subjected to addition of water and extracted with ethyl acetate. The organic phase was separated and then subjected to common work-up of washing, drying and concentration to obtain 17.84 g of crude 1-(2-propionyloxyethyl)cyclopropyl methanesulfonate (66% GC, yield 84%), containing 6.5% GC of 1-vinylcyclopropyl methanesulfonate generated by elimination of hydrogen chloride as a by-product and 18.1% GC of N,N-dimethylacetamide in addition to the target compound.

1-(2-Propionyloxyethyl)cyclopropyl methanesulfonate

Brown Oil
IR (D-ATR): ν=3022, 2979, 2943, 1733, 1352, 1189, 1163, 933 cm⁻¹.
¹H-NMR (500 MHz, CDCl₃): δ=0.73-0.77 (2H, m), 1.12 (3H, t, J=7 Hz), 1.26-1.30 (2H, m), 2.17 (2H, t, J=7 Hz), 2.32 (2H, q, J=7.5 Hz), 3.00 (3H, s), 4.72 (1H, s-like), 4.32 (2H, t, J=7.5 Hz) ppm.
¹³C-NMR (125 MHz, CDCl₃): δ=8.98, 11.50 (2C), 27.47, 35.03, 39.71, 60.91, 63.48, 174.29 ppm.

In the ¹³C-NMR spectrum, signals are overlapped due to the symmetry of the molecule. In the above, two methylene groups constituting the cyclopropyl ring are equivalent and give a signal assigned to two carbons. Hereinafter, the same is observed in the spectra of similar compounds.

GC-MS (EI, 70 eV): 29, 42, 57 (base peak), 83.
GC-MS (CI, isobutane): 141, 163, 237 [(M+H)⁺].

Example 2: Synthesis 2 of 1-(2-propionyloxyethyl)cyclopropyl methanesulfonate which the compound having Z=CH₃ and R¹=CH₃CH₂ in General Formula (2)

As shown in the following reaction equation, 1-(2-propionyloxyethyl)cyclopropyl methanesulfonate is synthesized from 1-(2-bromoethyl)cyclopropyl methanesulfonate.

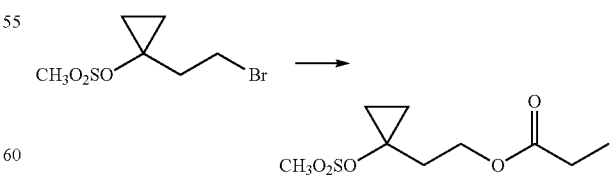

The reaction was carried out in the same manner as in Example 1 except that 30.0 g of 1-(2-bromoethyl)cyclopropyl methanesulfonate (75.2% GC) was used in the place of 1-(2-chloroethyl)cyclopropyl methanesulfonate to obtain 28.83 g of crude 1-(2-propionyloxyethyl)cyclopropyl methanesulfonate (72% GC, yield 90%) containing 5.5% GC of 1-vinylcyclopropyl methanesulfonate generated by elimination of hydrogen bromide as a by-product in addition to the target compound. The product was the same as the product in Example 1.

Example 3: Synthesis of 1-(2-propionyloxyethyl)cyclopropyl p-toluenesulfonate which is the compound having Z=p-CH$_3$—C$_6$H$_4$ and R$^1$=CH$_3$CH$_2$ in General Formula (2)

As shown in the following reaction equation, 1-(2-propionyloxyethyl)cyclopropyl p-toluenesulfonate is synthesized from 1-(2-chloroethyl)cyclopropyl p-toluenesulfonate.

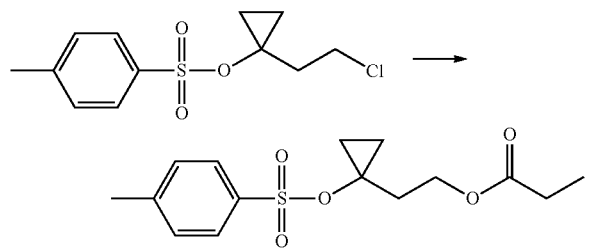

The reaction was carried out in the same manner as in Example 1 except that 25.0 g of 1-(2-chloroethyl)cyclopropyl p-toluenesulfonate (80% GC) was used in the place of 1-(2-chloroethyl)cyclopropyl methanesulfonate to obtain 33.83 g of crude 1-(2-propionyloxyethyl)cyclopropyl p-toluenesulfonate (53% GC, yield 79%).

1-(2-Propionyloxyethyl)cyclopropyl p-toluenesulfonate

Brown Oil

IR (D-ATR): v=2967, 2942, 2881, 1737, 1361, 1193, 1172, 932 cm$^{-1}$.

$^1$H-NMR (500 MHz, CDCl$_3$): δ=0.64-0.68 (2H, m), 1.08-1.16 (5H, m), 2.12 (2H, t, J=7 Hz), 2.28 (2H, q, J=7.5 Hz), 2.43 (3H, s), 4.24 (1H, t, J=7 Hz), 7.32 (2H, d-like, J=8 Hz), 7.76 (2H, d-like, J=8 Hz) ppm.

$^{13}$C-NMR (125 MHz, CDCl$_3$): δ=8.99, 11.33 (2C), 21.59, 27.47, 35.02, 60.96, 63.98, 127.52 (2C), 129.75 (2C), 174.28 ppm.

GC-MS (ET, 70 eV): 29, 57, 91 (base peak), 119, 139, 155, 174, 211.

GC-MS (CI, isobutane): 83, 141, 155, 174, 211, 313 [(M+H)$^+$].

Example 4: Synthesis of 1-(2-acetoxyethyl)cyclopropyl methanesulfonate which is the compound having Z=R$^1$=CH$_3$ in General Formula (2)

As shown in the following reaction equation, 1-(2-acetoxyethyl)cyclopropyl methanesulfonate is synthesized from 1-(2-bromoethyl)cyclopropyl methanesulfonate.

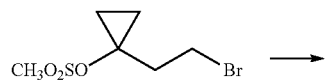

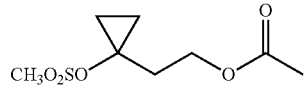

The reaction was carried out in the same manner as in Example 1 except that 10.0 g of 1-(2-bromoethyl)cyclopropyl methanesulfonate (76% GC) and 8.00 g of sodium acetate were used in the place of 1-(2-chloroethyl)cyclopropyl methanesulfonate and sodium propionate, respectively, to obtain 7.05 g of crude 1-(2-acetoxyethyl)cyclopropyl methanesulfonate (72% GC, yield 74%) containing 5.6% of 1-vinylcyclopropyl methanesulfonate generated by elimination of hydrogen bromide as a by-product in addition to the target compound.

1-(2-Acetoxyethyl)cyclopropyl methanesulfonate

Yellow Oil

IR (D-ATR): v=3023, 2968, 2941, 1737, 1345, 1193, 1164, 932 cm$^{-1}$.

$^1$H-NMR (500 MHz, CDCl$_3$): δ=0.73-0.77 (2H, m), 1.36-1.30 (2H, m), 2.04 (3H, s), 2.17 (2H, t, J=7 Hz), 3.00 (3H, s), 4.31 (1H, t, J=7 Hz) ppm.

$^{13}$C-NMR (125 MHz, CDCl$_3$): δ=11.49 (2C), 20.88, 34.99, 39.71, 61.05, 63.48, 170.89 ppm.

GC-MS (EI, 70 eV): 43 (base peak), 55, 67, 83, 101.

Comparative Example 1: Trial synthesis of 2-(1-hydroxycyclopropyl)ethyl propionate As shown in the following reaction equation, 2-(1-hydroxycyclopropyl)ethyl propionate is synthesized from 1-(2-chloroethyl)cyclopropanol, and 1-(2-propionyloxyethyl)cyclopropyl methansulfonate is further synthesized.

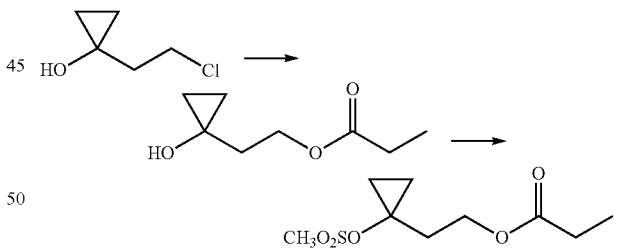

The reaction was carried out in the same manner as in Example 1 except that 11.7 g of 1-(2-chloroethyl)cyclopropanol (78% GC) was used in the place of 1-(2-chloroethyl) cyclopropyl methanesulfonate to attempt to synthesize 2-(1-hydroxycyclopropyl)ethyl propionate. Unfortunately, the resulting target compound has a polarity similar to that of N,N-dimethylacetamide as the solvent, so that the separation by solvent extraction was difficult. Regarding the synthesis of the 1-(2-acyloxyethyl)cyclopropyl sulfonate compounds (2), the results revealed that the method of acyloxylation of the 1-(2-haloethyl)cyclopropyl methanesulfonate, which is obtained by sulfonylation of 1-(2-chloroethyl)cyclopropanol, has advantages as shown in Examples 1 to 4.

Synthesis of 3-halomethyl-3-butenyl carboxylate represented by General Formula (3)

Example 5: Synthesis 1 of 3-bromomethyl-3-butenyl propionate which is the compound having $X^2$=Br and $R^1$=CH$_3$CH$_2$ in General Formula (3)

As shown in the following reaction equation, 3-bromomethyl-3-butenyl propionate is synthesized from 1-(2-propionyloxyethyl)cyclopropyl methanesulfonate.

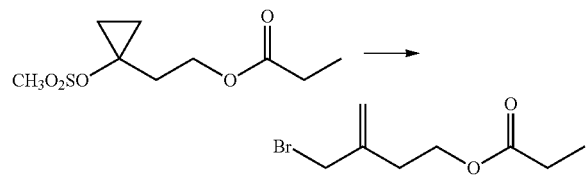

A mixture of 28.1 g of crude 1-(2-propionyloxyethyl) cyclopropyl methanesulfonate obtained in Example 2 and 100 ml of toluene was added dropwise to a solution of magnesium bromide in diethyl ether which was being stirred, heated and refluxed under a nitrogen atmosphere, wherein the solution of magnesium bromide in diethyl ether that had been prepared from 6.10 g of magnesium, 45.5 g of 1,2-dibromoethane and 100 ml of diethyl ether. The reaction mixture was refluxed for 2 hours, and then was stirred at room temperature for 13 hours. The reaction mixture was subjected to addition of a saturated aqueous ammonium chloride solution, and extracted with ethyl acetate. The organic phase was separated and then subjected to common work-up of washing, drying and concentration to obtain 22.59 g of crude 3-bromomethyl-3-butenyl propionate (78% GC, yield 96%).

3-Bromomethyl-3-butenyl propionate

Yellow Oil

IR (D-ATR): ν=2980, 2943, 1737, 1349, 1210, 1182, 1084, 914 cm$^{-1}$.

$^1$H-NMR (500 MHz, CDCl$_3$): δ=1.13 (2H, t, J=7.5 Hz), 2.31 (2H, q, J=7.5 Hz), 2.55 (2H, t-like, J=6.5 Hz), 4.01 (2H, s), 4.23 (1H, t, J=6.5 Hz), 5.01 (1H, s-like), 5.25 (1H, s) ppm.

$^{13}$C-NMR (125 MHz, CDCl$_3$): δ=9.08, 27.52, 32.53, 36.45, 61.99, 117.08, 141.75, 174.31 ppm.

GC-MS (EI, 70 eV): 41, 57 (base peak), 141, 221 (M$^+$).

Example 6: Synthesis 2 of 3-bromomethyl-3-butenyl propionate which is the compound having $X^2$=Br and $R^1$=CH$_3$CH$_2$ in General Formula (3)

As shown in the following reaction equation, 3-bromomethyl-3-butenyl propionate is synthesized from 1-(2-propionyloxyethyl)cyclopropyl p-toluenesulfonate.

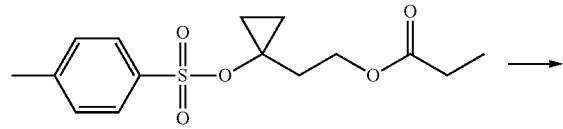

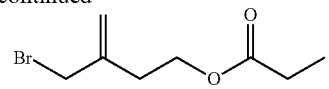

The reaction was carried out in the same manner as in Example 5 except that 20.0 g of crude 1-(2-propionyloxyethyl)cyclopropyl p-toluenesulfonate (53% GC) obtained in Example 3 was used in the place of crude 1-(2-propionyloxyethyl)cyclopropyl methanesulfonate obtained in Example 2 to obtain 15.8 g of crude 3-bromomethyl-3-butenyl propionate (53% GC). The crude product was distilled under reduced pressure to obtain 5.83 g of 3-bromomethyl-3-butenyl propionate (92% GC, yield 78%). The product was the same as the product in Example 5.

Example 7: Synthesis 1 of 3-bromomethyl-3-butenyl acetate which is the compound having $X^2$=Br and $R^1$=CH$_3$ in General Formula (3)

As shown in the following reaction equation, 3-bromomethyl-3-butenyl acetate is synthesized from 1-(2-acetoxyethyl)cyclopropyl methanesulfonate.

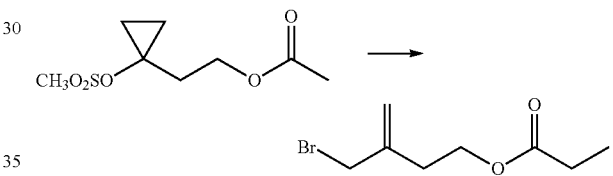

The reaction was carried out in the same manner as in Example 5 except that 6.58 g of crude 1-(2-acetoxyethyl) cyclopropyl methanesulfonate (72% GC) obtained in Example 4 was used in the place of crude 1-(2-propionyloxyethyl)cyclopropyl methanesulfonate obtained in Example 2 to obtain 5.58 g of crude 3-bromomethyl-3-butenyl acetate (77% GC, yield 97%).

3-Bromomethyl-3-butenyl acetate

Yellow Oil

IR (D-ATR): ν=2963, 1739, 1383, 1365, 1236, 1038, 915 cm$^{-1}$.

$^1$H-NMR (500 MHz, CDCl$_3$): δ=2.03 (3H, s), 2.54 (2H, t, J=7 Hz), 3.99 (2H, s), 4.22 (1H, t, J=7 Hz), 5.01 (1H, s-like), 5.25 (1H, s) ppm.

$^{13}$C-NMR (125 MHz, CDCl$_3$): δ=20.87, 32.45, 36.33, 62.12, 117.06, 141.66, 170.87 ppm.

GC-MS (EI, 70 eV): 43 (base peak), 67, 85, 97, 109, 127, 146, 163, 206 (M$^+$).

As a result of the spectral analyses of the 3-halomethyl-3-butenyl carboxylates synthesized in Examples 5 to 7, the isomerization of the exo-methylene at the 3-position into internal olefin, for example, the formation of 4-halo-3-methyl-2-butenyl carboxylates, was not observed. It is evident from the results that the synthetic method in accordance with the present invention achieves high selectivity.

Synthesis of 4-alkyl-3-methylenebutyl carboxylate represented by General Formula (5)

Example 8: Synthesis 1 of 7-methyl-3-methylene-7-octenyl propionate which is the compound having $R^2=CH_2=C(CH_3)-CH_2CH_2$ and $R^1=CH_3CH_2$ in General Formula (5)

As shown in the following reaction equation, 3-bromomethyl-3-butenyl propionate is reacted with 3-methyl-3-butenylmagnesium bromide to synthesize 7-methyl-3-methylene-7-octenyl propionate.

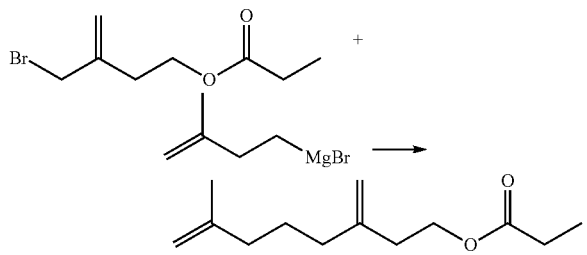

Under a nitrogen atmosphere, a mixture of 25.0 g of 3-methyl-3-butenyl bromide (83% GC), 2.50 g of 1,2-dibromoethane for activation of magnesium and 200 ml of tetrahydrofuran was added dropwise to a mixture of 4.40 g of magnesium and 10 ml of tetrahydrofuran to prepare a Grignard reagent, 3-methyl-3-butenylmagnesium bromide. While being stirred under a nitrogen atmosphere, the Grignard reagent was added dropwise to an ice-cooled mixture of 22.1 g of crude 3-bromomethyl-3-butenyl propionate synthesized in Example 5, 20 mg of copper(I) iodide, 30 mg of triethyl phosphite and 50 ml of tetrahydrofuran over 70 minutes, where the reaction temperature was maintained at 25° C. or less. The reaction mixture was stirred on ice for 1.5 hours, subjected to addition of a saturated aqueous ammonium chloride solution, and extracted with diethyl ether. The organic phase was separated and then subjected to common work-up of washing, drying, and concentration to obtain 22.77 g of crude 7-methyl-3-methylene-7-octenyl propionate. The crude product was distilled under reduced pressure to obtain 14.58 g of 7-methyl-3-methylene-7-octenyl propionate (95% GC, yield 85%).

7-Methyl-3-methylene-7-octenyl propionate

Colorless Oil
IR (D-ATR): v=3075, 2981, 2938, 1739, 1645, 1462, 1375, 1349, 1182, 1084, 889 cm$^{-1}$.
$^1$H-NMR (500 MHz, CDCl$_3$): δ=1.12 (3H, t, J=7.6 Hz), 1.53-1.61 (2H, m), 1.71 (3H, s), 1.97-2.06 (4H, m), 2.31 (2H, q, J=7.6 Hz), 2.33 (2H, t-like, J=7 Hz), 4.17 (2H, t, J=7.1 Hz), 4.67 (1H, s-like), 4.70 (1H, s-like), 4.77 (1H, s-like), 4.81 (1H, s-like) ppm.
$^{13}$C-NMR (125 MHz, CDCl$_3$): δ=9.10, 22.32, 25.51, 27.56, 34.95, 35.86, 37.29, 62.73, 109.96, 111.18, 145.44, 145.60, 174.41 ppm.
GC-MS (EI, 70 eV): 29, 41, 57 (base peak), 68, 79, 93, 107, 121, 136, 210 (M$^+$).

Example 9: Synthesis 2 of 7-methyl-3-methylene-7-octenyl propionate which is the compound having $R^2=CH_2=C(CH_3)-CH_2CH_2$ and $R^1=CH_3CH_2$ in General Formula (5)

As shown in the following reaction equation, 3-chloromethyl-3-butenyl propionate is synthesized from 1-(2-propionyloxy)cyclopropyl methanesulfonate, and 7-methyl-3-methylene-7-octenyl propionate is further synthesized.

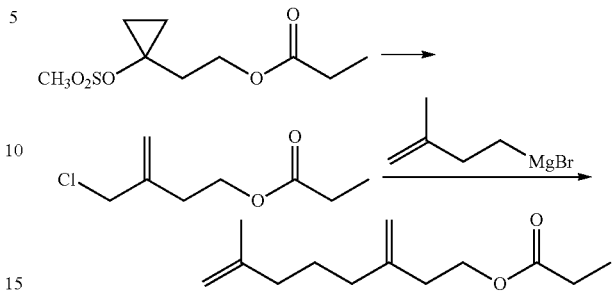

A mixture of 13.25 g of 1-(2-propionyloxyethyl)cyclopropyl methanesulfonate (88% GC) and 50 ml of dichloromethane was stirred on ice under a nitrogen atmosphere, while 25.0 g of titanium(IV) chloride was added dropwise thereto over 1 hour, keeping the reaction mixture at 20° C. or less. The temperature of the reaction mixture was increased to room temperature, and the mixture was stirred for 4 hours. Then the reaction mixture was re-cooled on ice, subjected to addition of water, and extracted with diethyl ether. The organic phase was separated and then subjected to common work-up of washing, drying and concentration to obtain 22.59 g of crude 3-chloromethyl-3-butenyl propionate (78% GC, yield 96%) as an intermediate.

The reaction and purification were carried out in the same manner as in Example 8 except that 10.20 g of crude 3-chloromethyl-3-butenyl propionate obtained above as the intermediate was used in the place of crude 4-bromomethyl-3-butenyl propionate synthesized in Example 5 to obtain 10.46 g of 7-methyl-3-methylene-7-octenyl propionate (97% GC, yield 99%). The product was the same as the product in Example 9.

Example 10: Synthesis of 3-propyl-3-butenyl acetate which is the compound having $R^2=CH_3CH_2$ and $R^1=CH_3$ in General Formula (5)

As shown in the following reaction equation, 3-bromomethyl-3-butenyl acetate is reacted with ethylmagnesium chloride to synthesize 3-propyl-3-butenyl acetate.

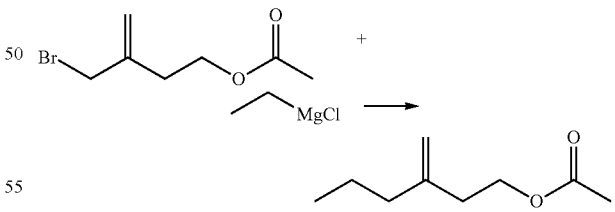

The target compound, 3-propyl-3-butenyl acetate, is a major component of the extract from exocrine glands of *Oechalia schellenbergii* (Heteroptera: Pentatomidae) that is a predaceous insect distributed in Australia and the South Pacific (J. R. Aldrich et al., Journal of Chemical Ecology, 22, 729 (1996)).

The reaction and purification were carried out in the same manner as in Example 9 except that 5.20 g of crude 3-bromomethyl-3-butenyl acetate (77% GC) synthesized in Example 7 and the Grignard reagent ethylmagnesium chloride were used in the place of crude 4-bromomethyl-3-butenyl propionate synthesized in Example 5 and the Grignard reagent 3-methyl-3-butenylmagnesium bromide used in Example 8, respectively, to obtain 2.76 g of 3-methylenehexyl acetate (90.1% GC, yield 86%).

3-Propyl-3-butenyl acetate

Colorless Oil

IR (D-ATR): ν=2960, 2933, 2874, 1743, 1365, 1237, 1035, 895 cm$^{-1}$.

$^1$H-NMR (500 MHz, CDCl$_3$): δ=0.89 (3H, t, J=7.7 Hz), 1.44 (2H, hex-like, J=7.7 Hz), 1.99 (2H, t, J=7.7 Hz), 2.03 (3H, s), 2.31 (2H, t, J=7.1 Hz), 4.15 (2H, t, J=7.1 Hz), 4.75 (1H, s-like), 4.79 (1H, s-like) ppm.

$^{13}$C-NMR (125 MHz, CDCl$_3$): δ=13.73, 20.70, 20.92, 34.79, 37.87, 62.90, 111.06, 145.42, 171.03 ppm.

GC-MS (EI, 70 eV): 43, 55, 68, 81 (base peak), 96, 111.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

The invention claimed is:

1. A 1-(2-acyloxyethyl)cyclopropyl sulfonate compound of General Formula (2):

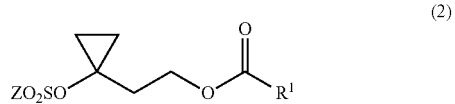

wherein R$^1$ is a monovalent hydrocarbon group having 1 to 10 carbon atoms and optionally containing one or more unsaturated bonds, and Z is a monovalent hydrocarbon group having 1 to 10 carbon atoms and optionally containing one or more unsaturated bonds.

* * * * *

UNITED STATES PATENT AND TRADEMARK OFFICE
CERTIFICATE OF CORRECTION

PATENT NO. : 9,688,622 B1
APPLICATION NO. : 15/436320
DATED : June 27, 2017
INVENTOR(S) : Kinsho et al.

It is certified that error appears in the above-identified patent and that said Letters Patent is hereby corrected as shown below:

On the Title Page

Item (65) Prior Publication Data:
Please insert -- US 2017/0158626 A1 June 8, 2017 --

Item (56) References Cited, Other Publications, Anderson et al. cite:
Please correct "1419-927" to read -- :919-927 --

Item (56) References Cited, Other Publications, Chong et al. cite:
Please correct "1-alkanois" to read -- 1-alkanols --

Item (56) References Cited, Other Publications, Bailey et al. cite:
Please correct "Pyroiysis" to read -- Pyrolysis --

In the Specification

Column 5, Line 40, equation (i):

Please correct " 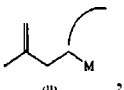 " to read --  --

Column 5, Line 55, equation (ii):

Please correct " 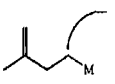 " to read --  --

Signed and Sealed this
Twenty-sixth Day of June, 2018

Andrei Iancu
*Director of the United States Patent and Trademark Office*

CERTIFICATE OF CORRECTION (continued)
U.S. Pat. No. 9,688,622 B1

Column 6, Line 5, equation (iii):

Please correct " 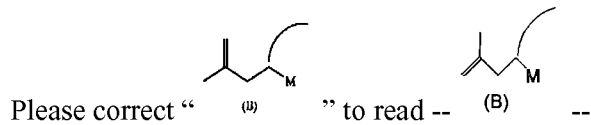 " to read -- --

Column 6, Line 5, equation (iii):

Please correct " 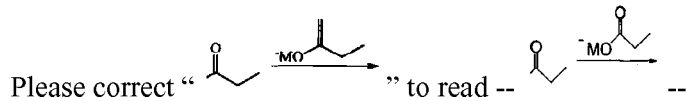 " to read -- --

Column 6, Line 20, equation (iv):

Please correct " 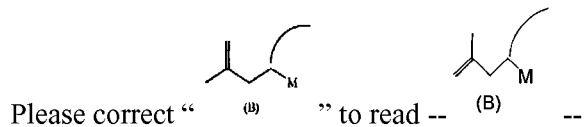 " to read -- --

Column 12, Line 40:
Please correct "copper (I) iodide" to read -- copper (II) iodide --